United States Patent [19]
Chanut

[11] Patent Number: 6,090,068
[45] Date of Patent: Jul. 18, 2000

[54] INJECTION AND PERFUSION DEVICE FOR USE IN AN IMPLANTABLE PORT ACCESS CATHETER

[76] Inventor: Stéphane Chanut, 20, Avenue Lespinasse, 93250 Villemomble, France

[21] Appl. No.: 09/349,763

[22] Filed: Jul. 9, 1999

[30] Foreign Application Priority Data

Jul. 23, 1998 [FR] France ................................. 98 09423

[51] Int. Cl.[7] ................................................ A61M 25/00
[52] U.S. Cl. ........................... 604/93; 604/173; 604/174
[58] Field of Search ............................. 604/93, 165, 175, 604/500, 502, 506, 507, 508, 523, 264

[56] References Cited

U.S. PATENT DOCUMENTS

| | | |
|---|---|---|
| 4,778,452 | 10/1988 | Moden et al. ........................ 604/93 |
| 4,969,870 | 11/1990 | Kramer et al. ..................... 604/93 X |
| 5,584,813 | 12/1996 | Livingston et al. . | |
| 5,637,088 | 6/1997 | Wenner et al. ................... 604/175 X |
| 5,968,011 | 10/1999 | Larsen et al. ......................... 604/93 |

FOREIGN PATENT DOCUMENTS

| | | |
|---|---|---|
| 0 281 421 | 9/1988 | European Pat. Off. . |
| 0 734 739 | 10/1996 | European Pat. Off. . |
| 2 725 902 | 4/1996 | France . |
| 2 752 164 | 2/1998 | France . |

*Primary Examiner*—John D. Yasko
*Attorney, Agent, or Firm*—Arent Fox Kintner Plotkin & Kahn, PLLC

[57] ABSTRACT

An injection and perfusion device which allows an easy extraction of the needle, with just one hand, and protection of the user by confinement of the needle. The needle support includes a base plate (1) with rebated guides (2) into which slides an attachable extraction device made up of a support block (6) into which is inserted a piston (9) which has a longitudinal groove (10) able to contain the vertical part of the angled needle (4).

7 Claims, 8 Drawing Sheets

INJECTION AND PERFUSION DEVICE FOR USE IN AN IMPLANTABLE PORT ACCESS CATHETER

The invention consists of a needle device for use in injections and perfusions into an implantable port access catheter which facilitates extraction and offers protection for the person handling the needle.

With the existing traditional devices, the user risks being harmed or contaminated by the needle because the action of withdrawing the needle requires the use of both hands, one of which has to be very close to the needle because it holds the implanted port access catheter in place under the skin. Often there is a rebound effect and the needle is exposed. The invented device resolves these difficulties and allows an easy extraction of the needle, with just one hand, while ensuring effective protection of the user.

Therefore the invention is essentially an injection and perfusion device for use in an implantable port access catheter consisting of a base plate in which a 90° angled needle with a perfusion tube attached to it is mounted, such base plate coming into contact with the patient's skin, device whereby the base plate is equipped to take an attachable extraction device made up of a support block into which is inserted a piston with a longitudinal cut-out able to cover the vertical part of the angled needle, such piston also being furnished with at least one element to block or lock with the base plate and support block.

According to a specific characteristic of the invention, the means by which the attachable extraction device is held in place consist of lateral parallel guides on the base plate, on either side of a cylindrical hole passing through the base plate and through which the vertical part of needle extends.

According to another specific characteristic of the invention, the support block has sides curving inwards with the concavity facing outwards, and at the base of these sides are flanges which slide into the grooves of the base plate. In addition, the support block has a cylindrical hole running through its whole length for the piston of a diameter the same as that of the hole of the base plate.

The specific characteristics and advantages of the invention will become apparent on reading the following description of a working example, given by way of example only and without limitation, and with reference to the diagrams annexed hereto.

The needle support is more specifically indicated in FIGS. 1 to 6 by the letter A.

The needle support comprises essentially a flat base plate 1, which can be of any shape, but here is presented as a rectangular flat base plate. This base plate holds a needle 4 with a 90° bend in it at the level of the base plate. One end of the needle points perpendicularly to the base plate; the other end is connected to a flexible tubing for connection 14. The base plate has in its centre a cylindrical hole 3 through which the needle 4 passes in its vertical section perpendicular to the base plate. On the upper surface of the base plate there are two lateral parallel guides 2 situated at each side of the hole 3 and lying parallel to the initial horizontal axis of the needle 4. The two guides are spanned at the farthest end by a border serving as a stop. A thin layer of foam rubber 5 is affixed to the periphery of the underside of the base plate 1.

An extraction device, indicated by the letter B, is mounted onto the needle support A. It is illustrated more specifically in FIGS. 7 to 10.

This extraction device is composed of a support block 6 generally of a parallelepipedal shape, two lateral uprights of which 15 are curved with the concavity facing outwards, allowing a firm finger grip. At the base of these lateral uprights 15, there are flanges 7 which are intended to slide into the rebated guides 2 on the base plate. The support block 6 has a cylindrical hole 13 bored through its centre lengthways of a diameter the same as that of the hole 3 in the base plate. In this hole can thus vertically slide a piston 9 which is at least twice as long as the vertical part of the needle 4. In the lower part of the piston 9 there is a longitudinal groove 10 which is very slightly wider than the external diameter of the needle 4, and which is longer than the vertical part of the needle. On the peripheral surface of the piston and approximately one-third from the bottom, pins 11 are situated for blocking and locking with the base plate and the support block. Lastly, a thumb-grip disc 16 is fixed to the top of the piston.

A protective layer of rubber 12 covers the end of the piston 9 to protect the patient's skin when pressure is applied. Around the inside edge of the hole 13 of the support block 6 there is a circular groove 8.

Figure 1:
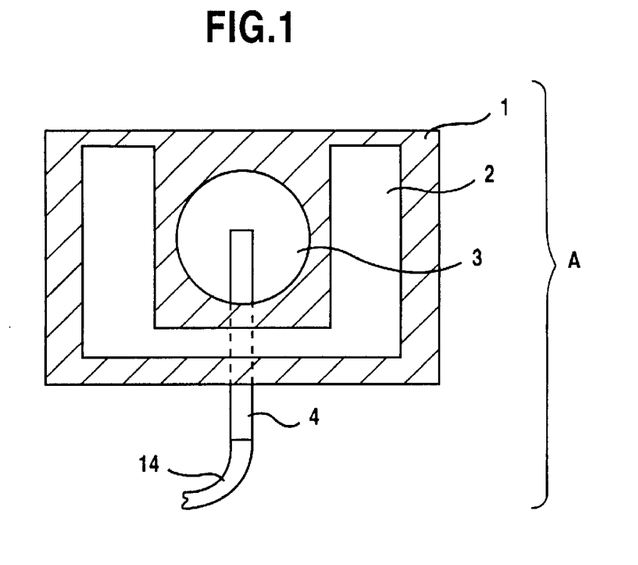
FIG. 1: view of the upper surface of the needle support.
Figure 2:
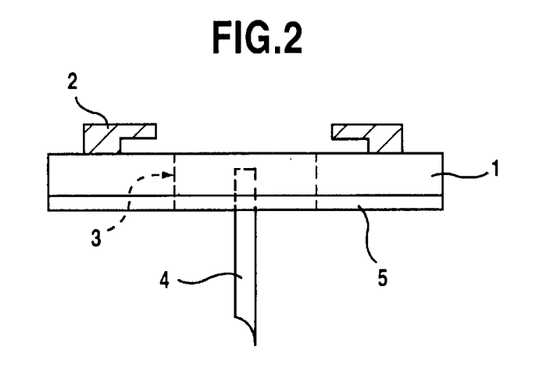
FIGS. 2, 3 and 4: respectively front, back and side views of the needle support.
Figure 3:
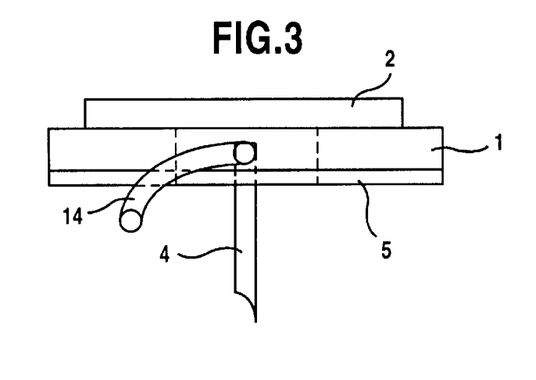
Figure 4:
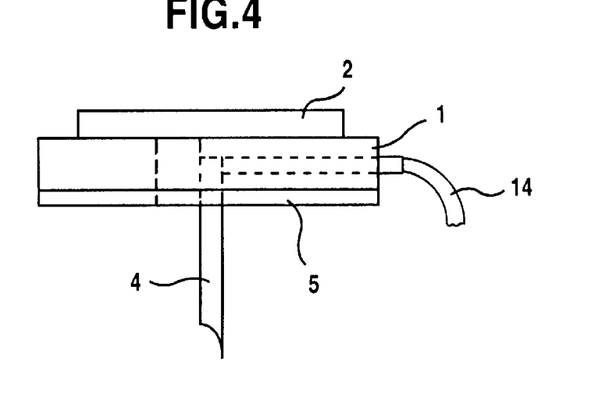
Figure 5:
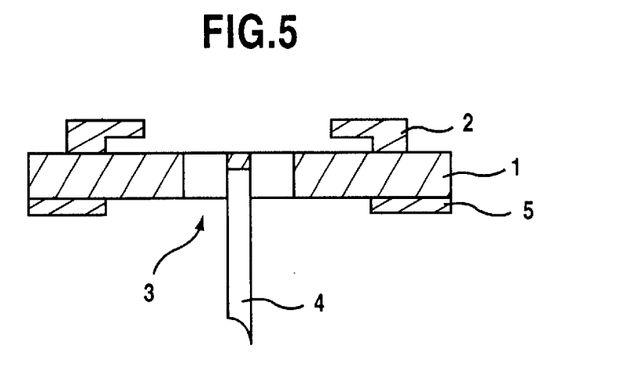
FIG. 5: front section of the needle support.
Figure 6:
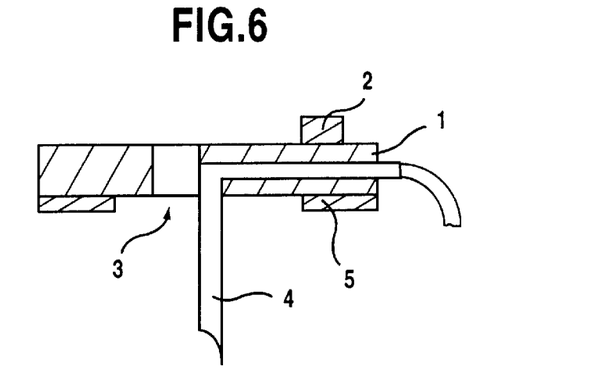
FIG. 6: transverse section of the needle support.
Figure 7:
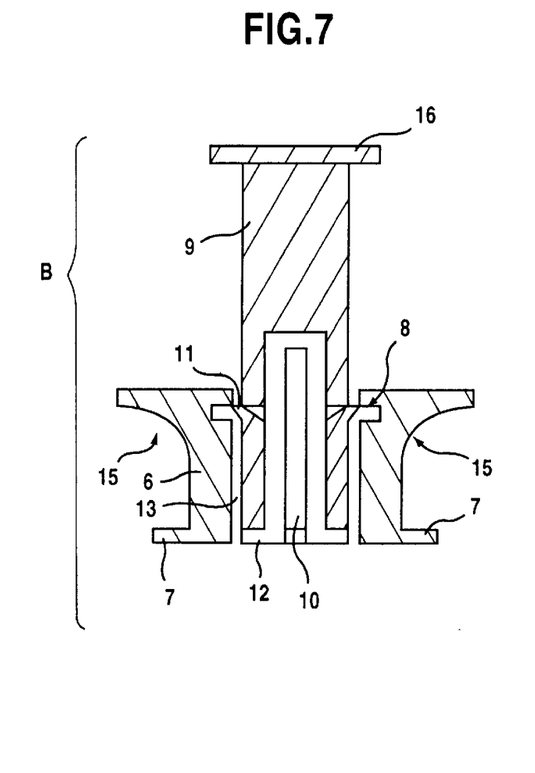
FIGS. 7 and 8: respectively front and transverse sections of the extraction device.
Figure 8:
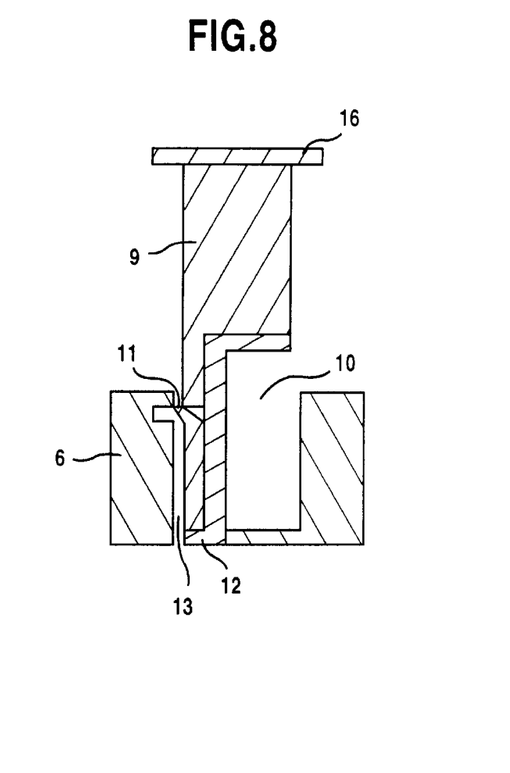
Figure 9:
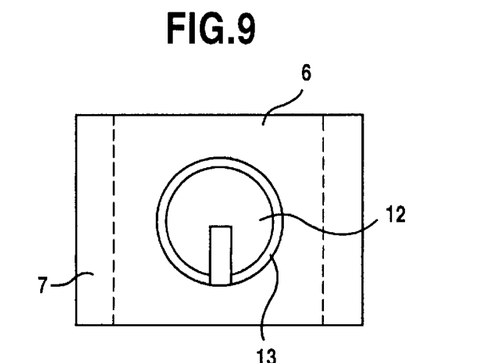
FIGS. 9 and 10: respectively underside and topside views of the extraction device.
Figure 10:
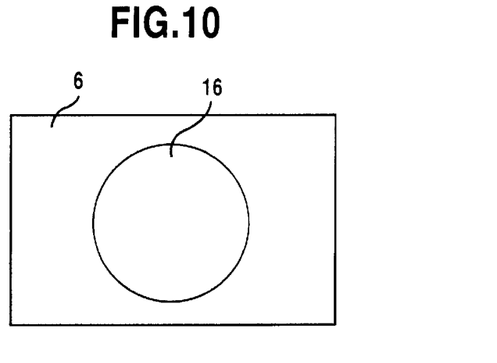
Figures 11, 12:
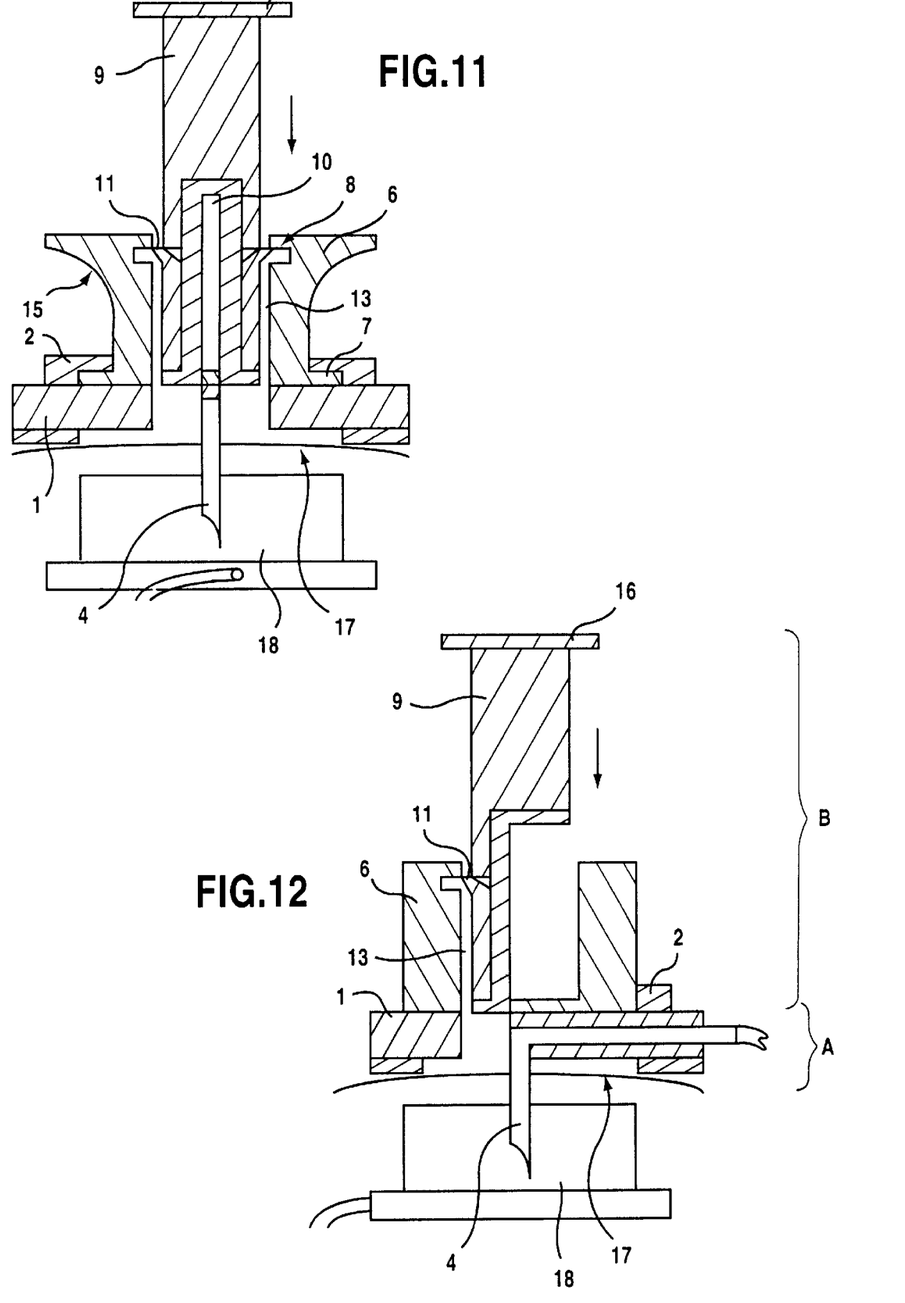
FIGS. 11 and 13: front sections of the extraction device fitted to the needle support in position for respectively injection and extraction.
FIGS. 12 and 14: transverse sections of the device as per FIGS. 11 and 13.

In FIGS. 11 and 12 it can be seen that the extraction device B has been mounted onto the needle support A by the flanges 7 of the support block 6 being slid into the rebated guides 2 of the base plate 1. The needle support A is applied to the patient's skin 17. The pins 11 fit into the groove 8 of the support block. The whole device is thus interlocked and the needle 4 has pierced the skin and reached the port access catheter 18 implanted under the skin for the injection or perfusion.

Figure 13:
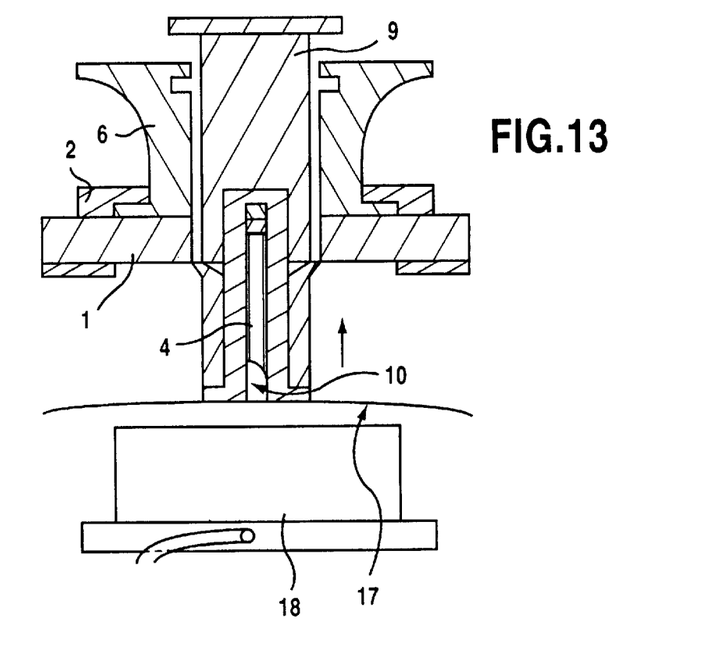
Figure 14:
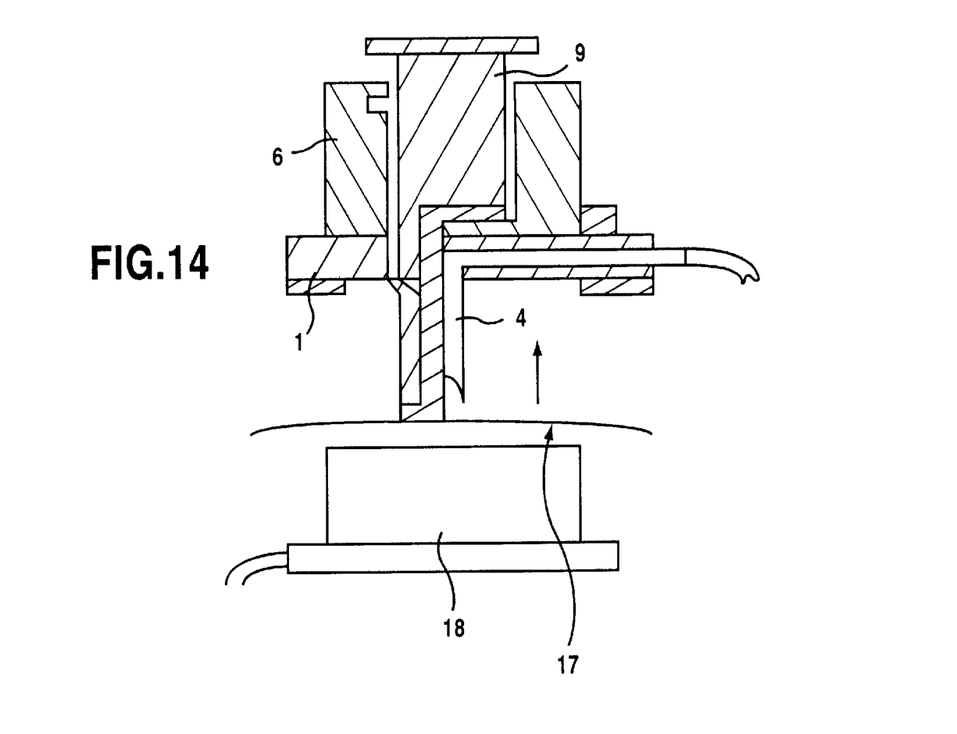

When the user wants to extract the needle from the port access catheter, he or she takes the support block 6 between the index and middle figure, squeezing the sides 15, then, with the thumb positioned on the disc 16, the user exerts pressure on the top of the piston 9. This movement pushes the piston down through the hole 13, and the protective layer 12 then presses against the patient's skin 17 and therefore on the top of the implantable port access catheter 18. While maintaining the pressure on the piston, the user pulls on the support block 6, by drawing the index and middle fingers towards the thumb, which results in causing simultaneously the base plate 1 to lift, the needle 4 to be extracted from the implantable port access catheter 18 and the patient's skin 17, as well as at the same time causing the vertical part of the needle to be retracted into the groove 10, thus protecting the user, as is shown in FIGS. 13 and 14.

In this position, the pins 11 are deployed just under the base plate 1, thus preventing the upwards motion of the piston 9 and therefore the release of the needle 4.

Figure 15:
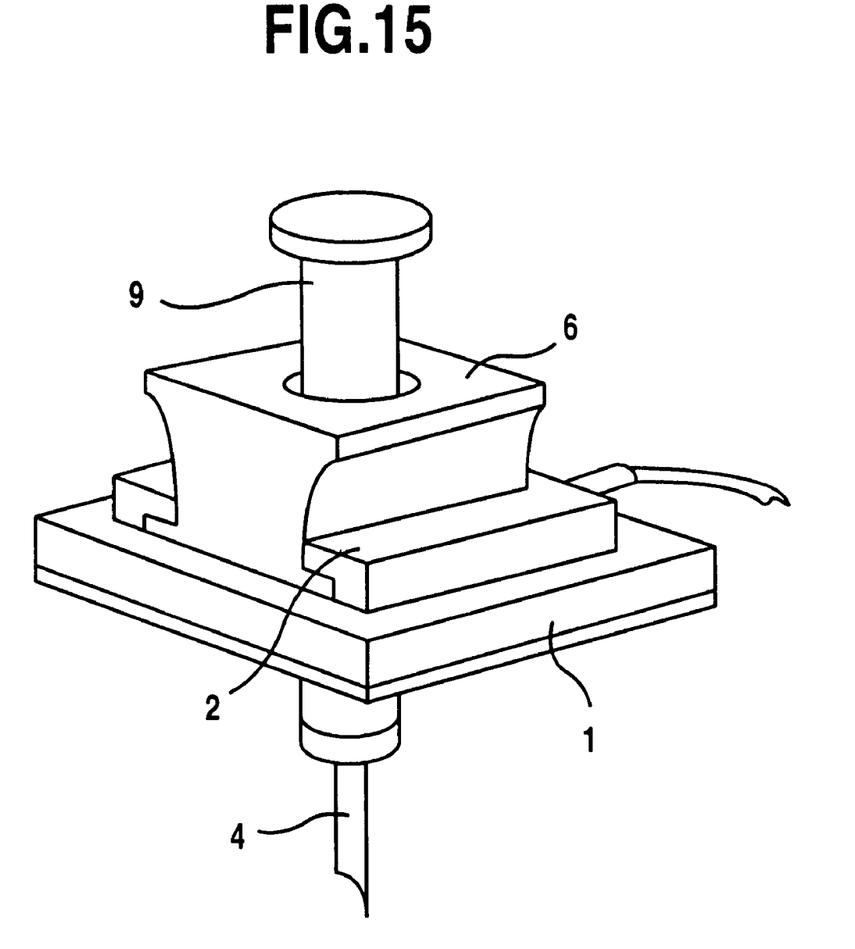
FIGS. 15: a pictorial drawing of the extraction device mounted on the needle support.

FIG. 15 shows the needle support with its base plate 1, interlocked with the support block 6, equipped with the piston 9, ready for extraction.

Figure 16:
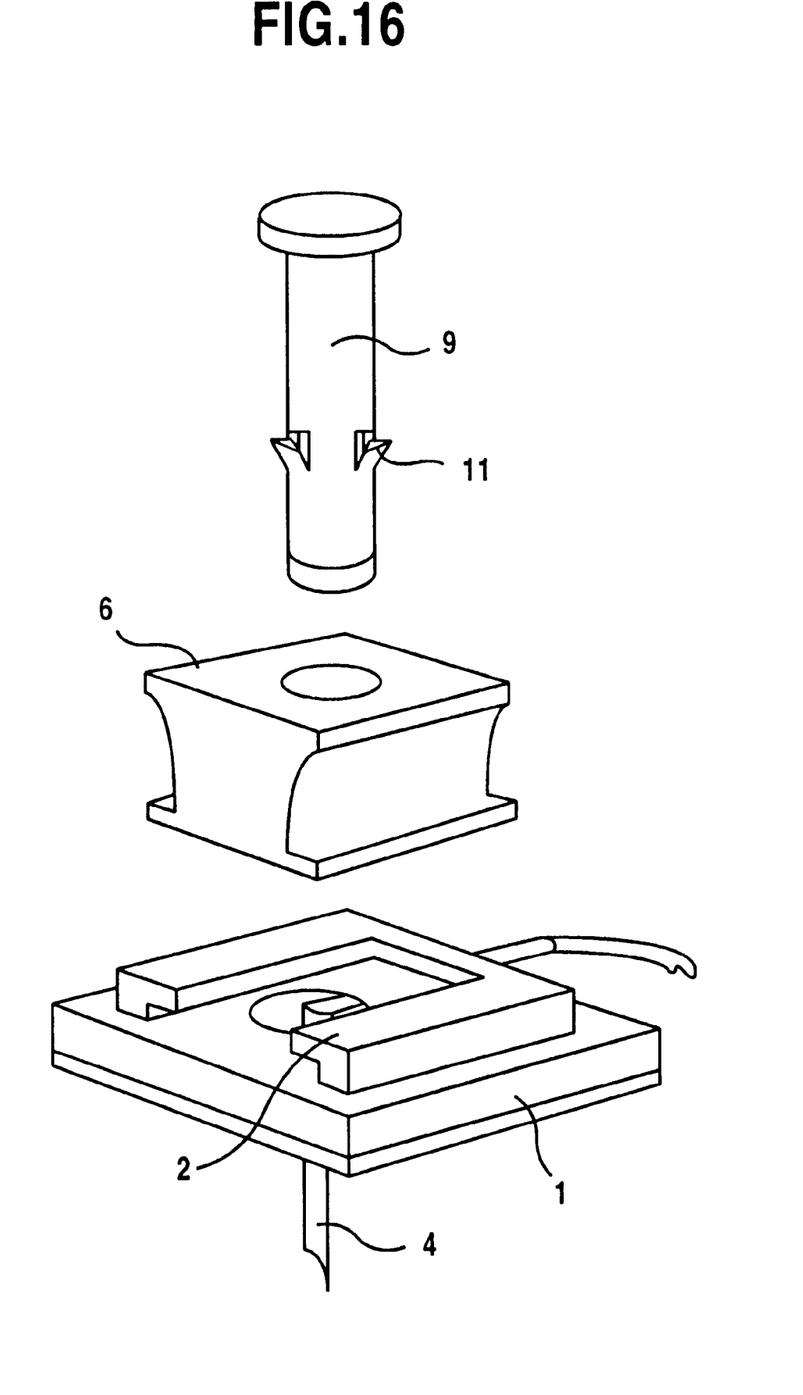
FIG. 16: an exploded pictorial view of the whole device.

FIG. 16 shows the device as a whole, the three elements being shown separated from one and another. The positioning of the pins 11 on the piston 9 can be seen clearly.

Figure 17:
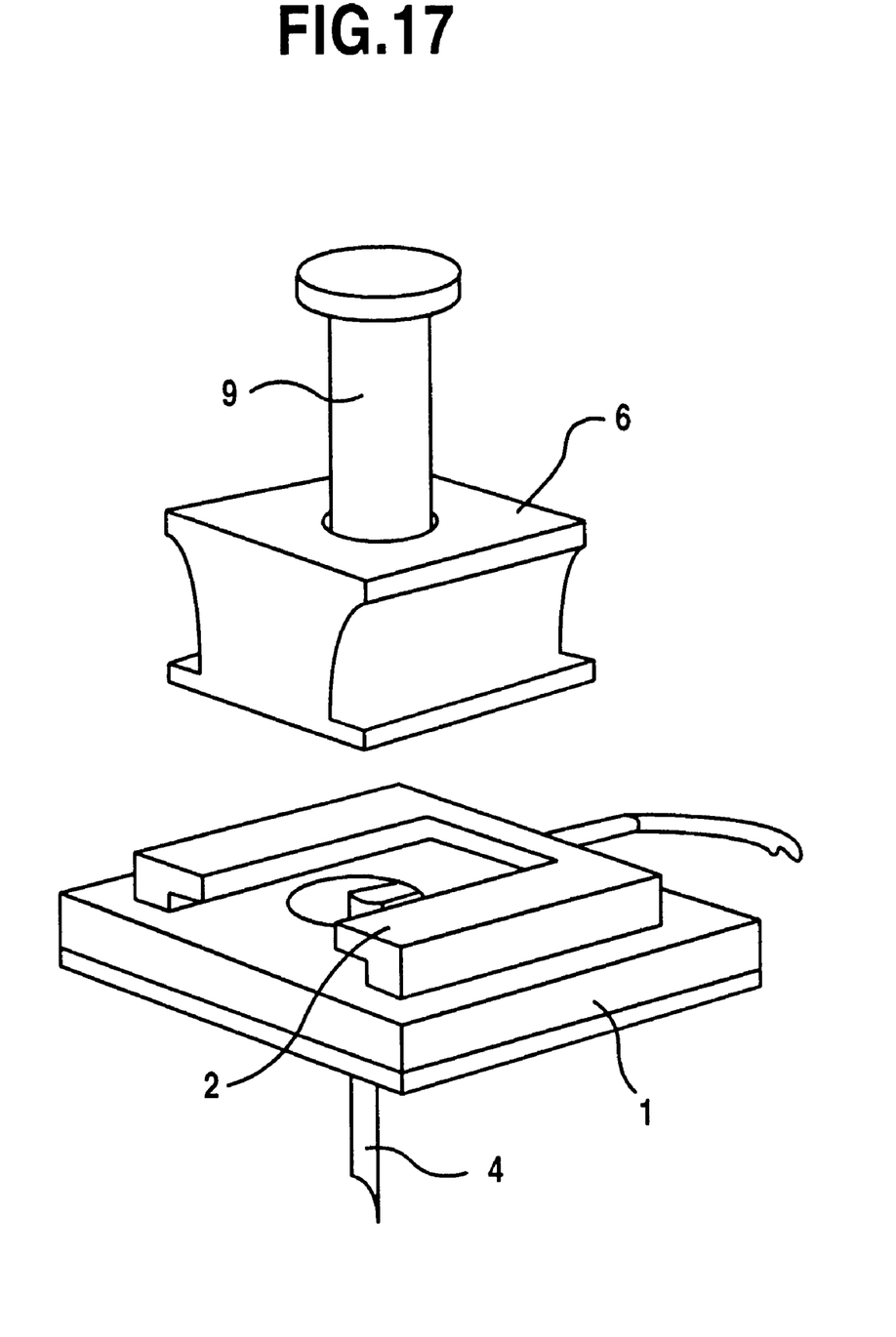
FIG. 17: a pictorial drawing of the extraction device separated from the needle support.

In FIG. 17, the piston is inserted into the support block.

What is claimed is:

1. Injection and perfusion device for use in an implantable port access catheter consisting of a base plate in which a 90° angled needle with a perfusion tube attached to it is mounted, such base plate adapted to come into contact with the patient's skin, characterised in that the base plate is equipped to take an attachable extraction device made up of a support block into which is inserted a piston with a longitudinal cut-out able to cover the vertical part of the angled needle, such piston also being furnished with at least one element to block or lock with the base plate and support block.

2. Injection and perfusion device according to claim 1, characterised in that the means by which the attachable extraction device is held in place consist of lateral parallel guides situated on the base plate on either side of a cylindrical hole passing through the base plate and through which the vertical part of needle extends.

3. Injection and perfusion device according to claim 1, characterised in that the support block has two curved lateral uprights with the concavity facing outwards, and in that at the base of these lateral uprights there are flanges which are intended to slide into the rebated guides 2 on the base plate.

4. Injection and perfusion device according to claim 1, characterised in that support block has a cylindrical hole running through its whole length for insertion of the piston, of a diameter the same as that of the hole of the base plate.

5. Injection and perfusion device according to the claims 1 and 4, characterised in that the blocking and locking mechanism consists of pins situated on the peripheral surface of the piston which slot into a circular groove for such purpose around the inside edge of the hole of the support block.

6. Injection and perfusion device according to claim 1, characterised by a protective rubber layer which covers the end of the piston.

7. Injection and perfusion device according to claim 1, characterised in that a thin layer of foam rubber covers the periphery of the underside of the base plate.

* * * * *